(12) United States Patent
Duncan

(10) Patent No.: US 11,660,451 B2
(45) Date of Patent: May 30, 2023

(54) FUNCTIONAL ELECTRICAL STIMULATION ERGOMETER INCLUDING AUTOMATIC SPASM CONTROL

(71) Applicant: Restorative Therapies, Inc., Baltimore, MD (US)

(72) Inventor: Michael Duncan, Lane Cove (AU)

(73) Assignee: RESTORATIVE THERAPIES, INC., Baltimore, MD (US)

( * ) Notice: Subject to any disclaimer, the term of this patent is extended or adjusted under 35 U.S.C. 154(b) by 252 days.

(21) Appl. No.: 17/113,697

(22) Filed: Dec. 7, 2020

(65) Prior Publication Data

US 2021/0330970 A1 Oct. 28, 2021

Related U.S. Application Data

(63) Continuation of application No. 16/242,624, filed on Jan. 8, 2019, now Pat. No. 10,857,359, which is a continuation of application No. 15/804,441, filed on Nov. 6, 2017, now Pat. No. 10,173,058.

(60) Provisional application No. 62/417,477, filed on Nov. 4, 2016.

(51) Int. Cl.

| | | |
|---|---|---|
| *A61N 1/36* | (2006.01) | |
| *A61B 5/11* | (2006.01) | |
| *A61N 1/372* | (2006.01) | |
| *A61N 1/18* | (2006.01) | |
| *A61N 1/32* | (2006.01) | |

(52) U.S. Cl.
CPC ............ *A61N 1/36003* (2013.01); *A61B 5/11* (2013.01); *A61N 1/36014* (2013.01); *A61N 1/37288* (2013.01); *A61B 5/1101* (2013.01); *A61N 1/18* (2013.01); *A61N 1/32* (2013.01); *A61N 1/36* (2013.01); *A61N 1/3603* (2017.08)

(58) Field of Classification Search
CPC ... A61N 1/18; A61N 1/32; A61N 1/36; A61N 1/36003; A61N 1/36014; A61N 1/3603; A61B 5/11; A61B 5/1101
See application file for complete search history.

(56) References Cited

U.S. PATENT DOCUMENTS

| | | |
|---|---|---|
| 2,109,188 A | 2/1938 | Bajanova |
| 3,310,817 A | 3/1967 | Harding |
| 3,488,088 A | 1/1970 | Goldberg et al. |
| 3,693,614 A | 9/1972 | Schon |
| 3,917,261 A | 11/1975 | Small et al. |
| 4,499,900 A | 2/1985 | Petrofsky et al. |

(Continued)

FOREIGN PATENT DOCUMENTS

| | | |
|---|---|---|
| CN | 201423119 Y | 3/2010 |
| DE | 2121877 A1 | 12/1972 |

(Continued)

OTHER PUBLICATIONS

Notification of Reasons for Refusal for Japanese Application No. 2019-521700, dated Oct. 12, 2021, 11 pages.

(Continued)

*Primary Examiner* — Joshua Lee
(74) *Attorney, Agent, or Firm* — Troutman Pepper Hamilton Sanders LLP (Rochester)

(57) ABSTRACT

This invention controls stimulation levels and cycling cadence on an FES ergometer to minimize or prevent the occurrence of spasm in spinal cord injured or other neurologically impaired patients.

20 Claims, 1 Drawing Sheet

(56) References Cited

U.S. PATENT DOCUMENTS

| | | | |
|---|---|---|---|
| 4,601,464 A | | 7/1986 | Mousel |
| 4,691,694 A | | 9/1987 | Boyd et al. |
| 5,244,441 A | * | 9/1993 | Dempster ............... A63B 23/00 |
| | | | 482/901 |
| 5,478,299 A | | 12/1995 | Harmon |
| 5,722,915 A | * | 3/1998 | Reck ................ A63B 21/00178 |
| | | | 482/4 |
| 6,010,468 A | | 1/2000 | Grove et al. |
| 6,152,855 A | | 11/2000 | Dean, Jr. et al. |
| 6,507,757 B1 | * | 1/2003 | Swain ................. A61N 1/36003 |
| | | | 607/49 |
| 6,695,795 B2 | | 2/2004 | Knoll |
| 8,788,049 B2 | * | 7/2014 | Lasko ................. A61N 1/36003 |
| | | | 607/48 |
| 8,905,951 B2 | | 12/2014 | Barriskill et al. |
| 9,511,256 B2 | | 12/2016 | Barriskill et al. |
| 10,173,058 B2 | | 1/2019 | Duncan |
| 10,857,359 B2 | | 12/2020 | Duncan |
| 2002/0026130 A1 | | 2/2002 | West |
| 2004/0023759 A1 | * | 2/2004 | Duncan .............. A61N 1/36003 |
| | | | 482/57 |
| 2004/0122483 A1 | | 6/2004 | Nathan et al. |
| 2005/0015118 A1 | * | 1/2005 | Davis ....................... A61H 1/02 |
| | | | 607/49 |
| 2005/0251067 A1 | | 11/2005 | Terry |
| 2006/0247095 A1 | | 11/2006 | Rummerfield |
| 2007/0112394 A1 | * | 5/2007 | Nathan ............... A61N 1/36014 |
| | | | 607/149 |
| 2007/0208392 A1 | | 9/2007 | Kuschner et al. |
| 2009/0012579 A1 | * | 1/2009 | Perumal ............. A61N 1/36003 |
| | | | 607/48 |
| 2010/0248903 A1 | | 9/2010 | Cardile |
| 2010/0262048 A1 | | 10/2010 | Shinomiya et al. |
| 2010/0331603 A1 | * | 12/2010 | Szecsi ....................... A61N 2/02 |
| | | | 482/57 |
| 2013/0053734 A1 | * | 2/2013 | Barriskill ............. A61H 1/0229 |
| | | | 601/5 |
| 2013/0053736 A1 | | 2/2013 | Konishi |
| 2013/0158622 A1 | | 6/2013 | Libbus et al. |
| 2013/0218247 A1 | | 8/2013 | Sachs |
| 2015/0148866 A1 | | 5/2015 | Bulsen et al. |
| 2015/0182784 A1 | | 7/2015 | Barriskill et al. |
| 2015/0190667 A1 | | 7/2015 | Balandis et al. |
| 2016/0016036 A1 | * | 1/2016 | Barriskill ........... A61N 1/36003 |
| | | | 482/57 |
| 2017/0303849 A1 | * | 10/2017 | De Sapio ........... A61N 1/36031 |
| 2019/0336759 A1 | | 11/2019 | Duncan |

FOREIGN PATENT DOCUMENTS

| | | |
|---|---|---|
| DE | 4113135 A1 | 10/1992 |
| DE | 202007013826 U1 | 3/2008 |
| JP | 2003-117006 A | 4/2003 |
| JP | 2003117006 A | 4/2003 |
| JP | 2006-000271 A | 1/2006 |
| JP | 2006000271 A | 1/2006 |
| JP | 2009-039454 | 2/2009 |
| RU | 2265461 C1 | 12/2005 |
| WO | WO 2018/085770 | 5/2018 |

OTHER PUBLICATIONS

Office Action for U.S. Appl. No. 13/219,610, dated Mar. 28, 2014, 10 pages.
Office Action for U.S. Appl. No. 14/563,320, dated Jun. 5, 2015, 7 pages.
Extended European Search Report for European Application No. 15168037.8, dated Oct. 16, 2015, 7 pages.
Office Action for European Application No. 15168037.8, dated Apr. 6, 2018, 6 pages.
Office Action for European Application No. 15168037.8, dated May 11, 2017, 6 pages.
Office Action for U.S. Appl. No. 14/713,915, dated Mar. 15, 2016, 5 pages.
International Search Report and Written Opinion for International Application No. PCT/US2017/060184, dated Mar. 5, 2018, 7 pages.
Extended European Search Report for European Application No. 17868179.7, dated Jun. 8, 2020, 9 pages.
Behrman, A. L. et al., "Locomotor Training After Human Spinal Cord Injury: A Series of Case Studies," Phys. Ther. 80(7):688-700 (Jul. 2000).
Belanger, M. et al., "Electrical Stimulation: Can It Increase Muscle Strength and Reverse Osteopenia in Spinal Cord Injured Individuals?," Arch. Med. Rehabil. 81:1090-1098 (Aug. 2000).
Colombo, G. et al., "Treadmill Training of Paraplegic Patients Using a Robothic Orthosis," J. Rehabil. Research and Dev. 37(6):693-700 (Nov./ Dec. 2000).
Daly, J. J. et al., "Therapeutic Neural Effects of Electrical Stimulation," IEEE Transactions on Rehabil. Eng. 4(4):218-230 (Dec. 1996).
Dietz, V. et al., "Locomotor Capacity of Spinal Cord in Paraplegic Patients," Ann. Neurol. 37(5):574-582 (May 1995).
Dobkin, B. et al., "Weight-supported treadmill vs. over-ground training for walking after acute incomplete SCI," Neurology 66:484-493 (2006).
Faghri, P. D. et al., "Functional electrical stimulation leg cycle ergometer exercise: training effects on cardiorespiratory responses of spinal cord injured subjects at rest and during submaximal exercise," Arch. Phys. Med. Rehabil. 73(11):1085-1093 (Nov. 1992).
Field-Fote, E. C. et al., "Locomotor Training Approaches for Individuals with Spinal Cord injury: A Preliminary Report of Walking-related Outcomes," J. Neurol. Phys. Therapy 29(3):127-137 (2005).
Frotzler, A. et al., "Effect of Detraining on Bone and Muscle Tissue in Subjects with Chronic Spinal Cord Injury After a Period of Electrically-Stimulated Cycling: A Small Cohort Study," J. Rehabil. Med. 41(4):282-285 (Apr. 2009).
Griffin, L. et al., "Functional Electrical Stimulation Cycling Improves Body Composition, Metabolic and Neural Factors in Persons with Spinal Cord Injury," J. Electromyog. Kinesiol., 19(4):614-622 (2008).
Hesse, S. et al., "A Mechanized Gait Trainer for Restoration of Gait," J. Rehabil. Res. and Dev. 37(6):701-708 (Nov./Dec. 2000).
Kinikou, M. et al., "Reflex Effects of Induced Muscle Contraction in Normal and Spinal Cord Injured Subjects," Muscle & Nerve, 26(3):374-382 (Sep. 2002).
McDonald, J. W. et al., "Late recovery following spinal cord injury. Case report and review of the literature," J. Neurosurg 97(2 Suppl. ):252-265 (Sep. 2002).
Mohr, T. et al., "Long-term adaptation to electrically induced cycle training in severe spinal cord injured individuals," Spinal Cord, 35(1):1-16 (Jan. 1997).
Shields, R. K. et al., "Musculoskeletal Plasticity After Acute Spinal Cord Injury: Effects of Long-Term Neuromuscular Electrical Stimulation Training," J. Neurolophysiology 95(4):2380-2390 (Apr. 2006).
Wernig, A. et al., "Laufband locomotion with body weight support improved walking in persons with severe spinal cord injuries," Paraplegia, 30(4):229-238 (Apr. 1992).
Wirz, M. et al., "Effectiveness of automated locomotor training in patients with chronic incomplete spinal cord injury: a multicenter trial," Arch. Phys. Med. Rehabil. 86(4):672-680 (Apr. 2005).
Office Action for U.S. Appl. No. 16/242,624, dated Apr. 8, 2020, 11 pages.
Office Action for Russian Application No. 2019106793, dated Mar. 24, 2021, 20 pages.
Examination Report for correspondence Australia Patent Application No. 2017354122 (dated Aug. 31, 2022).
Notification of Reasons for Refusal for corresponding Japan Patent Application No. 2019-521700 (dated Sep. 13, 2022).

* cited by examiner

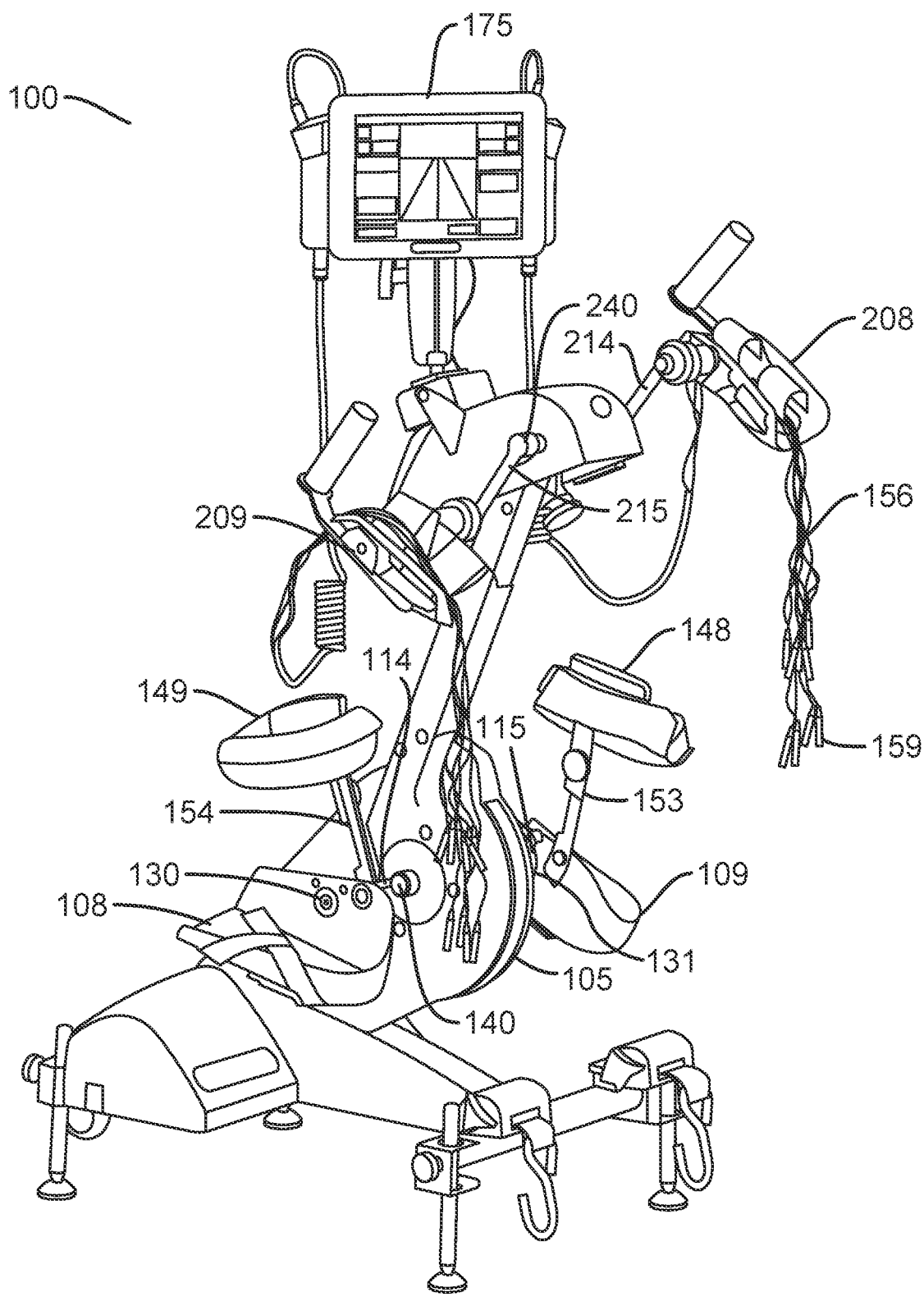

FUNCTIONAL ELECTRICAL STIMULATION ERGOMETER INCLUDING AUTOMATIC SPASM CONTROL

CROSS-REFERENCE TO RELATED APPLICATIONS

The present application is a continuation of U.S. patent application Ser. No. 16/242,624, entitled "Functional Electrical Stimulation Ergometer Including Automatic Spasm Control," filed Jan. 8, 2019, which is a continuation of U.S. patent application Ser. No. 15/804,441, entitled "Functional Electrical Stimulation Ergometer Including Automatic Spasm Control," filed Nov. 6, 2017, now U.S. Pat. No. 10,173,058, which claims priority to and the benefit of U.S. Provisional Application No. 62/417,477, filed Nov. 4, 2016, the disclosures of which are hereby incorporated herein in their entireties and for all purposes.

FIELD OF THE INVENTION

The invention relates to functional electrical stimulation (FES) systems for rehabilitation of individuals suffering from neurological injuries. More particularly, the present invention relates to a device that utilizes both mechanical and electrical stimulation of individual's muscles.

BACKGROUND OF THE INVENTION

Spinal cord injured patients gain great benefit from riding on FES enabled ergometers. However, when a patient's limbs are set in motion and/or when stimulation is applied at the start of a session many patients suffer from muscle spasms. This spasm often prevents the patients from riding for several minutes until the spasms have subsided. This can cause time to be lost by both the patient and therapist/caregiver and results in reducing the benefits that the patient receives from the FES ergometer.

Current techniques to minimize spasm include:

1. Stretching the patient's legs prior to riding. The problem with this approach is that it is labor intensive and does not always achieve the desired results.

2. Having the therapist observe the patient as stimulation is being applied and manually prevent the stimulation from increasing when the patient is showing early signs of spasm. The problem with this approach is that it requires a well-trained therapist to be present when the patient cycles. This is not always practical.

3. Setting the FES ergometer to increase the stimulation levels on the subject very slowly so that the patient's muscles accommodate the stimulation. The problem with this solution is that a therapist needs to be trained to know how to set-up the FES ergometer for a patient known to have spasms. Another problem is that it takes longer for the patient to receive the maximum benefit of FES cycling because the stimulation ramps up slowly. The patient may only occasionally suffer from spasm in which case it would be better to ramp up stimulation more quickly when the patient is not suffering from spasm.

BRIEF DESCRIPTION OF THE INVENTION

According to the invention, there is provided a functional electrical stimulation device having a left extremity support and a right extremity support, wherein both extremity supports are connected to a primary drive motor that causes the extremity supports to move in a reciprocal motion; the left extremity support is connected to a left extremity support servo motor and the right extremity support is connected to a right extremity support servo motor, wherein each of said right and left extremity support servo motors causes its respective extremity support to rotate about an axis. The device further has a control unit connected to the left and right extremity support servo motors which controls the actuation of the left and right extremity support servo motors. The control unit may also include functional electrical stimulation leads attached to skin adhesive electrodes which deliver electrical stimulation to a patient's muscles.

The device also includes an automatic spasm control system including a monitor which continuously monitors the torque required to rotate one or both of the left and right extremity supports and a controller configured to calculate a rate of change of said torque, and to calculate a maximum electrical stimulation, a maximum stimulation ramp-up rate, a maximum servo-motor speed and a maximum servo-motor ramp-up rate.

According to further embodiments, the functional electrical stimulation system has two drive arms connecting the primary drive motor to each of said left and right extremity supports, the drive arms optionally having various attachment points for connecting to corresponding right and left cranks at different attachment positions. According to further embodiments, the extremity supports are attached to the drive arms by the corresponding left and right cranks.

According to further embodiments of the invention, the controller of said automatic spasm control system is configured to identify a possible onset of spasm when a monitored amount of torque or rate of change of torque exceeds a predetermined value, and when a monitored amount of torque or rate of change of torque exceeds said predetermined value, to compare a current level of electrical stimulation to said calculated maximum stimulation and to compare a current crank speed to said calculated maximum crank speed and to send instructions to said control unit connected to the left and right extremity support servo motors and to said functional electrical stimulation leads to reduce the amount of electrical stimulation and crank speed.

According to further embodiments of the invention, there is provided a therapeutic muscle exercise device having a cycling base configured to accept a subject's upper or lower extremities and assist a subject in exercising the subject's muscles; the cycling base having a first extremity support and a second extremity support, wherein said extremity supports are driven or resisted by a motor controlled by a controller, the device further including a functional electrical stimulation controller, wherein the functional stimulation controller and the first and second extremity supports and cycling base are configured to assist a subject in moving his or her upper or lower extremities; said device further including an automatic spasm control system comprising a monitor configured to continuously monitor a torque required to rotate one or both of said left and right extremity supports, said controller configured to calculate a rate of change of said torque, a maximum servo-motor speed and a maximum servo-motor ramp-up rate, said functional electrical stimulation controller configured to calculate a maximum electrical stimulation, a maximum stimulation ramp-up rate.

According to further embodiments of the invention the controller manages isometric functional electrical stimulation to the subject's muscles.

According to further embodiments of the invention there is provided a method of exercising a subject's extremities comprising: placing the subject's extremities in an extremity support of a device described herein, placing electrical stimulation electrodes on the subject's extremities, and exercising the subject's extremities.

According to further embodiments of the invention, the exercising step includes actively assisting the subject in moving the subject's extremities by rotating the extremity supports around an extremity support pivot point.

According to further embodiments of the invention, the method includes assisting the subject to exercise the subject's extremities through isometric functional electrical stimulation.

According to further embodiments of the invention, the method includes increasing muscle electrical stimulation and reducing motor assistance.

According to further embodiments of the invention, electrical stimulation evokes coordinated muscle contractions and the extremity supports' do not drive rotation.

According to further embodiments of the invention, the method includes increasing motor assistance and decreasing electrical stimulation.

According to further embodiments of the invention, the automatic spasm controller is configured to identify a possible onset of spasm when a monitored amount of torque or rate of change of torque exceeds a predetermined value, and when a monitored amount of torque or rate of change of torque exceeds said predetermined value, and to compare a current crank speed to said calculated maximum crank speed and said electrical stimulation controller configured to compare a current level of electrical stimulation to said calculated maximum stimulation.

DESCRIPTION OF THE DRAWINGS

The subsequent description of the preferred embodiments of the present invention refers to the attached drawings, wherein:

FIG. 1 shows an RT300™ Functional Electrical Stimulation cycling system by Restorative Therapies, with an automatic spasm control system of the invention installed in the RT300™'s controller.

DETAILED DESCRIPTION OF THE INVENTION

The invention summarized above may be better understood by referring to the following description, the accompanying drawings, and the claims listed below. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form. While the invention is described herein in the context of an RT300-SLSA cycling system, it may be used in conjunction with any FES system, including the systems described in U.S. Pat. Nos. 8,905,951 and 9,511,256, the disclosures of which are incorporated herein in their entirety.

As shown in FIG. 1, one embodiment of the present invention comprises a therapeutic muscle exercise device 100 used to treat patients who may have partial or entire paralysis of the arms and/or legs. The device 100 comprises a cycling base 105 that is mounted on a mobile support 103.

The cycling base 105 has a first extremity support 108 and a second extremity support 109. It is contemplated that in some embodiments a single extremity support may be included to facilitate treatment of subjects who have lost a limb. Each extremity support 108 and 109 are attached to the cycling base by a first rotating arm 114 and a second rotating arm 115, respectively.

The rotating arms 114 and 115 attach to the extremity supports 108 and 109 at a extremity support pivot point 130 and 131. The configuration allows the foot of the subject to rotate as normally as it would when performing a cycling motion naturally. The rotating arms connect to the cycling base 105 at a base pivot point 140. In a preferred embodiment, the base pivot point 140 comprises a shaft that passes through a channel that extends through the base; the shaft connects the base end of the first rotating arm 114 to the base end of the second rotating arm 115. In such embodiment, the shaft then rotates uniformly around the base pivot point 140. In other embodiments, the rotating arms 114, 115 may connect to two independently rotatable shafts at the base pivot point 140 allowing the extremity supports 108 and 109 to rotate independently of one-another.

The cycling base 105 also includes two calf supports 148, 149. In some embodiments, the calf supports 148 and 149 are connected to the extremity supports 108 and 109 though an attachment link 153, 154. In other embodiments, the calf supports 148 and 149 may not be linked to the extremity supports 108 and 109.

The device 100 also includes a functional electrical stimulation controller 175. The controller 175 manages the electrical impulses provided to the subject's muscles through a series of leads 159, which are connected to the controller 175 through a lead cable 156. The controller 175 also controls a motor (not shown) that controls the speed of rotation of the rotating arms 114 and 115. The controller 175 coordinates the rotation of the rotating arms 114 and 115 in conjunction with functional electrical stimulation through the leads 159 depending on the level of need of the subject. In some instances, the controller 175 will direct full movement of the rotating arms 114 and 115 in conjunction with electrical stimulation resulting in fully FES evoked movement. In the alternative, the controller 175 may reduce the level of assistance provided by the motor and the electrical stimulation allowing volitional movement by the subject. In yet a further embodiment, the controller 175 will not provide any assistance in order to allow the subject to rotate the extremity supports 108, 109 without assistance. The controller 175 provides such assistance as needed by the subject and directed by the user.

Likewise, wrist and hand supports 208 and 209 may be provided and configured to attach to rotating arms 214 and 215 at base pivot point 240, and subsequent attachment to wrist and hand supports 208 and 209.

In one embodiment, a method for exercising a subject's extremities is provided. According to this embodiment, the system continuously rotates at the set speed and it either assists or resists the patient's efforts. The patient's efforts are either volitional or evoked by FES. In a first step of the method the system's motor moves the subject's extremities and the controller provides initial muscle electrical stimulation. This first step can be referred to as a warm up step. In a subsequent step, referred to as active transition, the controller increases muscle electrical stimulation and reduces motor assistance until the muscle takes over movement of the extremity supports or 100% stimulation threshold is reached. In a subsequent step, referred to as the active step, electrical stimulation evokes coordinated muscle contractions as the rotating arms 114 and 115 (and/or 214 and 215) turn around the pivot point 140 (and/or 240) resulting in the subject's muscles performing the cycling motion. The combination of the rotating arms 114 and 115 (and/or 214 and 215) connected at the pivot point 140 (and/or 240) is also referred to herein as the crank. Once muscle fatigue is reached and/or detected by the controller, electrical stimulation is reduced and the motor of the cycling base takes over for cycling motion. In a final step, referred to as cool down, the motor completely takes over cycling motion allowing subject's muscles to rest while permitting movement through the range of motion.

According to a further embodiment, an automatic spasm control feature of the present invention monitors the amount of torque required to move the patient's arms or legs from the beginning of the therapy session. The system also monitors the pattern and rate of change, or smoothness, of the required torque through each rotation of the ergometer crank. The automatic spasm control system of the invention uses increases in required torque as well as decreases in the smoothness of the required torque to detect muscle tone and to detect if a muscle spasm is occurring.

For each amount of muscle tone detected, the automatic spasm control system of the invention sets a maximum stimulation level, a maximum stimulation ramp-up rate, a maximum crank speed, and a crank ramp-up rate. If a full muscle spasm occurs, then the automatic spasm control system inhibits the motor from rotating the crank for a period of time, and then tries to start the therapy session again.

The following example follows a patient starting a leg therapy session and the stimulation level is increasing. If the patient experiences the onset of a spasm, the torque required to assist leg rotation will begin to fluctuate which fluctuation in torque will be detected by the automatic spasm control system. Similarly, if the patient starts to exhibit high muscle tone, the motor torque required to assist the leg crank rotation will increase and the automatic spasm control system will detect this increase. In either event, automatic spasm control system will calculate the maximum stimulation level and cycling cadence appropriate to prevent the muscle tone from increasing or developing into a muscle spasm.

If the current therapy is stimulating at a higher level than the calculated maximum stimulation level appropriate to prevent the muscle tone from increasing or developing into a spasm, the automatic spasm control system will cause the stimulation level to be decreased accordingly. Likewise, if the current leg therapy cadence is currently going faster than the maximum cycling cadence to prevent the muscle tone from increasing or developing into a spasm, the automatic spasm control system will cause the cadence rate to be reduced.

Conversely, if the current stimulation level is lower than the calculated maximum stimulation value, then the system will calculate the maximum stimulation level ramp up rate that is appropriate to prevent the muscle tone from increasing or a muscle spasm from developing. The system will allow the stimulation level to increase at a rate no greater than this maximum.

If the cadence is lower than the calculated maximum cycling cadence value, then the system will calculate the maximum speed ramp up rate that is appropriate to prevent the muscle tone from increasing or a muscle spasm from occurring. The system will allow the cadence to increase at a rate no greater than this calculated maximum rate.

If the muscle tone continues to increase, then all of these maximum levels will be further reduced. This acts to allow the patient's muscles to accommodate the stimulation so that eventually the muscle tone will reduce. As the muscle tone reduces, the system will increase all these maximum levels. Once there is no or minimal muscle tone, no limits are imposed by the system. At this point the FES therapy session will continue using its preset stimulation level and cadence parameters.

In the event that the detected muscle tone does not decrease over time, indicating that the muscles are either not accommodating the prescribed cadence or stimulation levels, the automatic spasm control system will slowly allow a higher cadence and stimulation level. This allows a patient to progress to active cycling even though he/she is exhibiting tone. In this case it is likely that the detected tone was caused not by spasm, but by another factor such as myotatic reflex. According to various different embodiments of the invention, the system may make adjustments to cadence and stimulation levels appropriately for spasm and myotatic reflex.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

The invention claimed is:

1. A system, comprising:
an extremity support configured to receive an upper or lower extremity of a subject;
a motor assembly configured to control a speed and direction of reciprocal motion of the extremity support via a crank;
a control unit operatively coupled to the motor assembly and configured to control the motor assembly to cause the extremity support to move the upper or lower extremity of the subject, the control unit including functional electrical stimulation leads configured to be coupled to the subject such that electrical stimulation can be delivered to muscles of the patient via the functional electrical stimulation leads; and
an automatic spasm control system configured to:
continuously monitor a torque required for the motor assembly to move the extremity support and to calculate a rate of change of the torque,
identify that a monitored amount of torque required for the motor assembly to move the extremity support or a rate of change of torque required for the motor assembly to move the extremity support exceeds a predetermined value, and in response to identifying that the monitored amount of torque or the rate of change of torque exceeds the predetermined value, send instructions to the control unit to change a speed of the crank while maintaining a direction of reciprocal motion of the extremity support and to change an amount of electrical stimulation delivered via the functional electrical stimulation leads while continuing to deliver electrical stimulation.

2. The system of claim 1, wherein the automatic spasm control system is further configured to calculate a maximum speed of the crank, a maximum ramp-up rate of the crank, a maximum electrical stimulation, and a maximum stimulation ramp-up rate to prevent at least one of a muscle tone of the subject from increasing or a spasm of the subject from occurring.

3. The system of claim 2, wherein, if, after the automatic spasm control system sends the instructions, an amount of muscle tone of the subject increases, the automatic spasm control system is configured to reduce at least one of the maximum speed of the crank, the maximum ramp-up rate of the crank, the maximum electrical stimulation, or the maximum stimulation ramp-up rate.

4. The system of claim 2, wherein, if, after the automatic spasm control system sends the instructions, an amount of muscle tone of the subject reduces, the automatic spasm control system increases at least one of the maximum speed of the crank, the maximum ramp-up rate of the crank, the maximum electrical stimulation, and the maximum stimulation ramp-up rate.

5. The system of claim 2, wherein, if, after the automatic spasm control system sends the instructions, the amount of muscle tone of the subject does not decrease over a predetermined period of time, the automatic spasm control system increases the maximum crank speed and maximum electrical stimulation.

6. The system of claim 1, wherein the automatic spasm control system is further configured to:
calculate a maximum electrical stimulation to prevent at least one of a muscle tone of the subject from increasing or a spasm of the subject from occurring, and
compare a current level of electrical stimulation to the calculated maximum electrical stimulation, the instructions including instructions to reduce the amount of electrical stimulation delivered via the functional electrical stimulation leads if the current level of electrical stimulation is higher than the calculated maximum electrical stimulation.

7. The system of claim 1, wherein the automatic spasm control system is further configured to:
calculate a maximum electrical stimulation to prevent at least one of a muscle tone of the subject from increasing or a spasm of the subject from occurring, and
compare a current level of electrical stimulation to the calculated maximum electrical stimulation, the instructions including instructions to increase the amount of electrical stimulation delivered via the functional electrical stimulation leads at a rate equal to or less than the maximum stimulation ramp-up rate if the current level of electrical stimulation is lower than the calculated maximum electrical stimulation.

8. The system of claim 1, wherein the automatic spasm control system is further configured to:

calculate a maximum speed of the crank to prevent at least one of a muscle tone of the subject from increasing or a spasm of the subject from occurring,
compare a current crank speed to the calculated maximum speed of the crank, the instructions including instructions to reduce the speed of the crank if the current crank speed is higher than the calculated maximum speed of the crank.

9. The system of claim 1, wherein the automatic spasm control system is further configured to:
calculate a maximum speed of the crank to prevent at least one of a muscle tone of the subject from increasing or a spasm of the subject from occurring,
compare a current crank speed to the calculated maximum speed of the crank, the instructions including instructions to increase the speed of the crank at a rate equal to or less than the maximum ramp-up rate of the crank if the current crank speed is lower than the calculated maximum speed of the crank.

10. A system, comprising:
an extremity support configured to receive an upper or lower extremity of a subject;
a motor assembly configured to control a speed and direction of reciprocal motion of the extremity support via a crank;
a control unit operatively coupled to the motor assembly and configured to control the motor assembly to cause the extremity support to move the upper or lower extremity of the subject, the control unit including functional electrical stimulation leads configured to be coupled to the subject such that electrical stimulation can be delivered to muscles of the patient via the functional electrical stimulation leads; and
an automatic spasm control system configured to detect muscle tone by continuously monitoring a torque required for the motor assembly to move the extremity support and calculating a rate of change of the torque, the automatic spasm control system configured to calculate, for each of a plurality of amounts of muscle tone of the subject detected by the automatic spasm control system, a maximum crank speed and a maximum electrical stimulation,
the automatic spasm control system configured to:
detect an amount of muscle tone from the plurality of amounts of muscle tone of the subject by identifying that a monitored amount of torque required to rotate the extremity support or a rate of change of torque required to rotate the extremity support exceeds a predetermined value, and
in response to detecting the amount of muscle tone from the plurality of amounts of muscle tone, compare a current crank speed to the calculated maximum crank speed associated with the amount of muscle tone and a current level of electrical stimulation to the calculated maximum electrical stimulation associated with the amount of muscle tone.

11. The system of claim 10, wherein, if the current crank speed is higher than the calculated maximum crank speed associated with the amount of muscle tone, the automatic spasm control system is further configured to send instructions to the control unit to reduce a speed of the crank.

12. The system of claim 10, wherein the automatic spasm control system is configured to calculate, for each of the plurality of amounts of muscle tone of the subject detected by the automatic spasm control system, a maximum crank ramp-up rate, and, if the current crank speed is lower than the calculated maximum crank speed associated with the amount of muscle tone, the automatic spasm control system is further configured to send instructions to the control unit to increase the speed of the crank at a rate equal to or less than the maximum crank ramp-up rate associated with the amount of muscle tone.

13. The system of claim 10, wherein, if the current level of electrical stimulation is higher than the calculated maximum electrical stimulation associated with the amount of muscle tone, the automatic spasm control system is further configured to send instructions to the control unit to reduce the amount of electrical stimulation delivered via the functional electrical stimulation leads.

14. The system of claim 10, wherein the automatic spasm control system is configured to calculate, for each of the plurality of amounts of muscle tone of the subject detected by the automatic spasm control system, a maximum stimulation ramp-up rate, and, if the current level of electrical stimulation is lower than the calculated maximum electrical stimulation associated with the amount of muscle tone, the automatic spasm control system is further configured to send instructions to the control unit to increase the amount of electrical stimulation delivered via the functional electrical stimulation leads at a rate equal to or less than the calculated maximum stimulation ramp-up rate associated with the amount of muscle tone.

15. A method, comprising:
continuously monitoring a torque required for a motor assembly to move an extremity support coupled to the motor assembly via a crank, the extremity support configured to receive an upper or lower extremity of a subject;
calculating a rate of change of the torque;
identifying that a monitored amount of torque required for the motor assembly to move the extremity support or a rate of change of torque required for the motor assembly to move the extremity support exceeds a predetermined value, and
in response to identifying that the monitored amount of torque or the rate of change of torque exceeds the predetermined value, sending instructions to a control unit operatively coupled to the motor assembly to change a speed of the crank while maintaining a direction of reciprocal motion of the extremity support and to change an amount of electrical stimulation delivered via the functional electrical stimulation leads while continuing to deliver electrical stimulation.

16. The method of claim 15, further comprising:
calculating a maximum speed of the crank, a maximum ramp-up rate of the crank, a maximum electrical stimulation, and a maximum stimulation ramp-up rate to prevent at least one of a muscle tone of the subject from increasing or a spasm of the subject from occurring.

17. The method of claim 15, further comprising:
calculating a maximum electrical stimulation to prevent at least one of a muscle tone of the subject from increasing or a spasm of the subject from occurring, and
comparing a current level of electrical stimulation to the calculated maximum electrical stimulation, the instructions including instructions to reduce the amount of electrical stimulation delivered via the functional electrical stimulation leads if the current level of electrical stimulation is higher than the calculated maximum electrical stimulation.

18. The system of claim 15, further comprising:
calculating a maximum electrical stimulation to prevent at least one of a muscle tone of the subject from increasing or a spasm of the subject from occurring, and
comparing a current level of electrical stimulation to the calculated maximum electrical stimulation, the instructions including instructions to increase the amount of electrical stimulation delivered via the functional electrical stimulation leads at a rate equal to or less than the maximum stimulation ramp-up rate if the current level of electrical stimulation is lower than the calculated maximum electrical stimulation.

19. The system of claim 15, further comprising:
calculating a maximum speed of the crank to prevent at least one of a muscle tone of the subject from increasing or a spasm of the subject from occurring, and
comparing a current crank speed to the calculated maximum speed of the crank, the instructions including instructions to reduce the speed of the crank if the current crank speed is higher than the calculated maximum speed of the crank.

20. The system of claim 15, further comprising:
calculating a maximum speed of the crank to prevent at least one of a muscle tone of the subject from increasing or a spasm of the subject from occurring,
comparing a current crank speed to the calculated maximum speed of the crank, the instructions including instructions to increase the speed of the crank at a rate equal to or less than the maximum ramp-up rate of the crank if the current crank speed is lower than the calculated maximum speed of the crank.

* * * * *